(12) United States Patent
Axelsson et al.

(10) Patent No.: US 11,547,470 B2
(45) Date of Patent: Jan. 10, 2023

(54) ENDOSURGICAL DEVICE AND METHOD OF USE

(71) Applicant: MULTI4 AB, Jonkoping (SE)

(72) Inventors: Robert Axelsson, Granna (SE); Ronny Brakhya, Huskvarna (SE); Henrik Vagerstam, Perstorp (SE); Miden Melle Hannah, Jonkoping (SE)

(73) Assignee: MULTI4 AB, Jonköping (SE)

( * ) Notice: Subject to any disclaimer, the term of this patent is extended or adjusted under 35 U.S.C. 154(b) by 0 days.

(21) Appl. No.: 16/955,725

(22) PCT Filed: Dec. 14, 2018

(86) PCT No.: PCT/SE2018/051315
§ 371 (c)(1),
(2) Date: Jun. 18, 2020

(87) PCT Pub. No.: WO2019/125289
PCT Pub. Date: Jun. 27, 2019

(65) Prior Publication Data
US 2020/0375655 A1 Dec. 3, 2020

(30) Foreign Application Priority Data
Dec. 22, 2017 (SE) .................................. 1751639-4

(51) Int. Cl.
*A61B 18/14* (2006.01)
*A61B 10/06* (2006.01)
*A61B 18/00* (2006.01)

(52) U.S. Cl.
CPC .......... *A61B 18/1447* (2013.01); *A61B 10/06* (2013.01); *A61B 2018/00083* (2013.01);
(Continued)

(58) Field of Classification Search
CPC ................ A61B 10/06; A61B 18/1447; A61B 2018/00196
See application file for complete search history.

(56) References Cited

U.S. PATENT DOCUMENTS 5,354,311 A * 10/1994 Kambin ................. A61B 17/29
600/564
5,482,054 A * 1/1996 Slater .................... A61M 1/774
600/564

(Continued)

FOREIGN PATENT DOCUMENTS

WO WO2006078743 A1 7/2008

OTHER PUBLICATIONS

International Search Report and Written Opinion Appl. No. PCT/SE2018/051315 dated Feb. 19, 2019.

*Primary Examiner* — Linda C Dvorak
*Assistant Examiner* — Ryan T Clark
(74) *Attorney, Agent, or Firm* — Kagan Binder, PLLC (57) ABSTRACT

An endosurgical device is provided. The endosurgical device comprises a flexible tube having at least two lengthwise extending channels, an end effector comprising two opposite jaws having opposite cutting edges, an effector sleeve that surrounds the tube at least at the distal tube end, and means for reciprocating the end effector axially in relation to the effector sleeve to close the jaws when the effector sleeve is moved forward and backwards to close and open the jaws, respectively. The exterior face of the opposite jaws is electrically insulated, and an electrical cord for providing current to the end effector extends inside one of the lengthwise extending channels of the tube. The endosurgical device may allow the surgeon to take several tissue specimens from an organ and to perform several functionalities when the device is inside the organ.

5 Claims, 7 Drawing Sheets (52) U.S. Cl.
CPC .............. *A61B 2018/00196* (2013.01); *A61B 2018/00517* (2013.01); *A61B 2018/00595* (2013.01); *A61B 2018/00982* (2013.01); *A61B 2018/1452* (2013.01)

(56) References Cited

U.S. PATENT DOCUMENTS

| | | | | |
|---|---|---|---|---|
| 5,746,740 | A * | 5/1998 | Nicholas | A61B 10/06 606/205 |
| 5,922,002 | A * | 7/1999 | Yoon | A61F 6/206 606/170 |
| 6,425,910 | B1 * | 7/2002 | Hugueny | A61B 10/06 606/206 |
| 2002/0188294 | A1 | 12/2002 | Couture | |
| 2006/0178699 | A1 | 8/2006 | Surti | |
| 2007/0055172 | A1 * | 3/2007 | Ratnakar | A61B 10/06 600/564 |
| 2010/0121153 | A1 * | 5/2010 | To | A61B 17/3417 600/214 |
| 2011/0237975 | A1 * | 9/2011 | Secrest | A61B 10/06 600/565 |
| 2014/0046323 | A1 | 2/2014 | Payne et al. | |
| 2014/0323910 | A1 * | 10/2014 | Lee | A61B 10/06 600/564 |
| 2017/0290602 | A1 * | 10/2017 | Germain | A61B 17/320016 |

* cited by examiner

ENDOSURGICAL DEVICE AND METHOD OF USE

CLAIM OF BENEFIT TO PRIOR APPLICATIONS

This application is a 371 filing of International Patent Application PCT/SE2018/051315 filed Dec. 14, 2018, which claims the benefit of SE1751639-4 filed Dec. 22, 2017, the entire content of which is expressly incorporated herein by reference thereto.

TECHNICAL FIELD

The present invention relates to an endosurgical device, comprising:
  a flexible tube having a distal tube end, a proximal tube end, and at least two lengthwise extending channels,
  an end effector comprising two opposite jaws having opposite cutting edges, which end effector is provided at the distal tube end,
  an effector sleeve that surrounds the tube at least at the distal tube end, and
  means for reciprocating the end effector axially in relation to the effector sleeve, or vice versa, to open and close the jaws.

BACKGROUND OF THE INVENTION

Urinary bladder cancer is one of the most expensive forms of cancer in Sweden and internationally, In the United States estimated costs are about 140,000 dollars per newly diagnosed person. Every year there are about 2,400 new persons in Sweden diagnosed with urinary bladder cancer. In the past 20 years, the number of cases has increased by a total of 35 percent and urinary cancer affects men three times as often as women. Cancer in the urinary bladder and urinary tract is the third most common form of cancer in men in Sweden.

About 70% of patients have a superficial urinary bladder cancer form restricted to the mucosa. This means that these patients can be cured, but unfortunately there is a risk of recurrence and of residual tumor. About two thirds of patients need a new surgery. It is not uncommon for one and the same patient to undergo several operations, sometimes only a few months after the first. There will be many regular visits to the urologist to discover recurrence early so that the cancer does not grow.

Cystoscopy is the primary diagnostic modality for the diagnosis of bladder carcinoma. A conventional cystoscope normally has two ports, an optical port that permits to see inside the bladder and a port for insertion of various devices.

If a cancer or a suspicious area is seen during the cystoscopy the patient is normally planned for a surgery at an operation theatre and then stays one night at the urology ward. In Sweden the patient needs to wait for about two weeks for this surgery and normally the patient receives a spinal anesthesia or general anesthesia before the procedure can be performed at a surgery department. During surgery biopsy specimens are taken with rigid metal instruments or a transurethral resection is performed also with rigid metal instruments. At some hospitals, biopsies can be performed as an outpatient procedure with flexible cystoscope but since the quality of the tissue specimens are not good enough with flexible biopsy instruments, rigid instruments that have a larger diameter need to be used to receive better tissue specimens and to be able to resect the cancer.

During cystoscopy, when there is suspicion of cancer in the bladder, the urologist generally obtains multiple bladder tissue specimens, typically using punch biopsy forceps, from various locations in the bladder to help establish the diagnosis and to determine the extent of a potential tumor. Generally, tissue specimens are taken from any areas of abnormal-looking urothelium and from suspected tumor areas, but typically from trigone, bladder dome, and right, left, anterior and posterior bladder walls. At the time of the procedure, the bladder is lavaged with fluid. Prior to tissue acquisition during a transurethral bladder biopsy using a flexible cystoscope local anesthesia is made at the sample site or anesthesia is obtained locally by instilling anesthetic agents into the bladder. Following tissue acquisition, the biopsy site is cauterized for hemostasis, and the procedure is repeated. Because a conventional cystoscope only has one working channel for the various devices needed during the surgical procedure, each of these various devices is moved in and out of the working channel each time a tissue specimen is taken from the bladder. Today it is not possible to only use one instrument to give anesthesia, take one or multiple biopsies, stop bleedings, and destruct small cancers in the bladder. Also because of the small dimensions the quality of the biopsy is not good enough because the important layers in the bladder wall needed to be seen in the microscope is not included. Since biopsies are taken today by pulling out the instruments when the jaws get caught in the tissue, the edges of the tissue sample are destroyed, and the quality of the tissue samples is decreased and can't be used to diagnose the cancer accurate.

There are many different categories of staff involved in the treatment of patients with superficial bladder cancer and costs are high. Today, taking tissue specimens from the urinary bladder cancer in an operating room at a surgery department is between 24,000 SEK and 32,000 SEK per patient. The patient is scheduled for surgery, is fastening, put under anesthetic, and operated with the rigid metal devices. A urinary catheter is inserted to drain blood and the patient is monitored at the ward 24 hours.

If the tissue specimen can be taken in a gentle biopsy procedure on an office as an outpatient procedure instead, without general anesthesia and without the need for a subsequent urinary catheter, the costs of the surgery is only 3,600 SEK per patient plus the device cost. So lots of cost can be saved if the biopsy procedure can be optimized.

The article "A system of multiple biopsy forceps", by Thomas V. Taylor, Curr. Surg. 2004 November-December; 61(6): pages 594-596 describes a new system of flexible endoscopic biopsy forceps, that should take larger and less traumatized biopsies than existing single biopsy forceps. The device utilizes a central wire with a barbed spike at one end, to which sliding sprung steel jaws are attached. An outer plastic sleeve surrounds the central wire, and conventional-type handles activate the jaws.

This known device is passed along the biopsy channel of a fiberoptic endoscope, and the tissue to undergo biopsy is visualized. Opening and closing of the forceps occurs when the outer sleeve slides on the inner wire allowing the sprung steel jaws to open and close. With the jaws open, the barb is pushed into the tissue to undergo biopsy. The fishhook-like barb pulls back the tissue into the jaws, which bite the tissue at an optimal angle and can thus obtain cleaner and bigger tissue specimens. For the second biopsy, the jaws are simply reopened, and as the barbed spike again pierces the tissue, the first specimen is pushed along the central wire. Up to 6 biopsies are to be stored in this way with a single passage of the biopsy forceps through the endoscope. All tissue specimens are retracted all together with the device when said device is retracted from the fiberoptic endoscope. However, the fishhook-like barb injures the tissue specimen and must be teased off the fishhook-like barb with another pair of forceps, or the tip of the barb is pushed into a piece of cork and the specimens cut off. Both ways downsize each tissue specimen, thereby affecting specimen integrity and casting doubt on precise origin. So because the tissue specimen needs to be manipulated off the barb the origin of the specimens can be difficult to keep under control and. Furthermore the barb-type kind of biopsy device is rather brutal to both patient and the tissue specimens, has no means for local anesthesia, no means for stopping local bleeding at the sampling site, and since 6 tissue specimens are stored along the barb simultaneously the front end must be rather large.

The article "Flexible cystoscopic bladder biopsies: a technique for outpatient evaluation of the lower urinary tract urothelium" by Marc Beaghler and Michael Grasso in Urology. 1994 November; 44(5):756-9. describes a monopolar techniques to obtain biopsies requiring an active electrical cord that adapts to the biopsy forceps and a standard electrocautery device, A grounding pad is placed on the patient's thigh. To obtain a biopsy, the forceps is advanced through the working channel of the cystoscope. The target area is engaged by toothed jaws of a forceps under direct vision and coagulation current is applied while withdrawing to cause blanching of the surrounding urethelium. The cystoscope and the tissue specimen are removed as one unit, and the cystoscope is reinserted to inspect biopsy site, bleeding and to take further tissue specimens.

European patent no. EP 1838229 B1 proposes biopsy forceps that includes a sheath and a rigid inner stainless steel shaft slidably disposed within the sheath, and having an end configured with a plurality of grasping members. The grasping members are movable between an open configuration and a closed configuration when the shaft and sheath moves. The grasping members have a curvilinear profile and are biased outwardly from the longitudinal axis when in the open configuration. The grasping members are unrestricted by the sheath when in the open configuration and is constrained by the sheath when in the closed configuration. The plurality of grasping members, which have proximal edges adapted for shearing, grasping, tearing, or cutting tissue, can be formed by laser-cutting the end of the shaft, and so that when they are in a closed configuration, they form a receptacle for retaining one or more tissue specimens. The shaft can be connected to an electrocautery device to energize the shaft to electrosurgically cut the tissue. This known biopsy forceps device may also be operably connected to an infusion source or a suction source. A suction source in form of a vacuum pump or a syringe is suggested connected to the shaft to assist in tissue removal or general fluid removal around the biopsy site, or to pull the tissue specimen back into the shaft for removal or for taking multiple biopsy samples. Alternative lumens are briefly suggested in addition to the single lumen shaft which must be used alternating, EP 1838229B1 is silent of how the grasping members manage to hold several tissue specimens at a time, thus how the grasping members can be opened without the sample inside the closed grasping members drops out again.

It is thus known that tissue specimens can be resected or excised using various kinds of effector tool, the most common being forceps. Monopolar electrocautery systems have been introduced in cystoscopy in attempts to reduce the risk of complications and produce better tissue specimens for the pathologist however until now these monopolar electrocautery systems tend to apply too much heat to the tissue specimen, which destroys the cancer cells and makes the tissue specimen unusable for cancer diagnostics.

There is a need within the art for an improved endosurgical device for a taking of tissue specimens from a hollow organ, body cavity or a tissue surface via an access channel.

SUMMARY OF THE INVENTION

In a main aspect of the present invention is provided an endosurgical device of the kind mentioned in the opening paragraph, which device has multiple functions that can be activated while the device is still inserted in the endoscope so that the device need not to be moved in and out of the endoscope many times for completing the required numbers of biopsies in a non-destructive and safe manner.

In yet an aspect of the present invention is provided an endosurgical device in form of an endoscopic biopsy forceps that are simple, cheap to produce, and disposable.

In yet an aspect of the present invention is provided a multi-functional endosurgical device for taking several tissue specimens, in particular for taking tissue specimens from the urinary bladder.

The novel and unique whereby these and other aspects are achieved according to the present invention consists in that
  the end effector of the endosurgical device comprises a
    main tubular body having a first end connected to the
    distal tube end to provide fluid communication to the at
    least two lengthwise extending channels, and an opposite second end having the opposite jaws,
  at least one of the jaws is arranged to diverge from a
    longitudinal axis of the end effector in a relaxed condition when the end effector is at least partly outside the
    effector sleeve.
  the end effector and the jaws are arranged so that the jaws
    are subjected to a compression force by the effector
    sleeve to keep the gap between the jaws closed to define
    a closed biopsy cup when the end effector is at least
    partly inside the effector sleeve,
  the exterior faces of the opposite jaws are electrically
    insulated, and
  an electrical cord for providing current to the end effector
    extends inside one of the lengthwise extending channels.

The endosurgical device can advantageously be used without general anesthesia on an out-patient or on a patient at the receiving ward. The endosurgical device allows the surgeon to take several tissue specimens directly from the suspicious target area without having to repeat inserting a series of different tools into the working channel of the endoscope for each taking of a tissue specimen. Cancer cells can be destructed in same surgical procedure while the endosurgical device is still inside the patient. The patient can go home immediately afterwards, needs no catheter, nor fasting before the surgical biopsy procedure.

The exterior faces of the opposite jaws are electrically insulated exteriorly to constitute a diathermy device that allows the tissue specimens to release from the organ, By using the term "diathermy" in the context of the present invention is meant that the jaws of the endosurgical devices are adapted to generate heat in organ tissue by high-frequency electromagnetic currents. The high-frequency electromagnetic currents pass through tissue and make a precise surgical incision like a scalpel blade, whereby the surgical diathermy provides fine, precise incisions and tissue specimens with hemostasis.

The jaws pinch the tissue specimen and in the diathermy step the jaws gently sever the tissue specimen from the organ, sear and/or cauterize the wound left at the biopsy site to stop bleeding. in this manner the tissue specimen releases from the organ and do not stick to the jaws. The tissue specimen becomes freely accommodated and protected between the jaws inside the biopsy cup defined by the closed jaws when the end effector is inside the effector sleeve. The effector sleeve presses and holds the jaws tight together to close the biopsy cup around the tissue specimen in a substantially leak-proof manner.

The electric insulation of the exterior faces of the jaws may preferably be obtained by providing a coating to said exterior surfaces. Such coating may preferably be a low friction coating, e.g. a Parylene® coating or a coating of Diamond-like carbon (DLC), that easily can be deposited on a conductive surface of the jaws, such as a metal surface, the metal being e.g. nitinol, aluminium or stainless steel. The trade name Parylene® covers chemical vapor deposited poly(p-xylylene) polymers often used as moisture and dielectric barriers. Within the scope of the present invention other kinds of insulating coatings can also be used.

The tube may be a non-conductive flexible tube, such as a plastic tube, and said thin flexible tube may be surrounded by a reinforcing member to provide the endosurgical device with sufficient structure to be guided along the working channel of the endoscope.

The effector sleeve can be reciprocated to open and close the jaws. In the alternative the end effector can be reciprocated in and out of the effector sleeve to open and close the jaws. in the closed position of the jaws wherein the end effector is fully inside the effector sleeve, the effector sleeve effectively seals any gaps between the opposite jaws, seals gaps where the jaws and the hinge members are free of the main tubular body, and any gap between the opposite cutting edges of the jaws to the extent possible. The effector sleeve may be a steel sleeve of be elastic to improve sealing capacity. A firm fit around the tube may suffice to obtain sufficient sealing.

In an advantageous embodiment both of the jaws are arranged to diverge from a longitudinal axis of the end effector in a relaxed condition when the end effector is at least partly outside the effector sleeve so that the jaws can span a large tissue specimen. Two opposite diverging jaws may e.g. open about 5 mm.

In a preferred embodiment the tube can have at least a first lengthwise extending channel for an effector wire that serve to keep the jaws in place when the effector sleeve is reciprocated. In the alternative the effector wire may serve for pulling the end effector inside the effector sleeve. The effector wire may be the electrical cord for supplying current to the end effector. Alternatively, the electrical cord may be provided in a separate second lengthwise extending channel of the tube. In the alternative the effector sleeve can be reciprocated by means of a reinforcing member surrounding the tube and being joined end-to-end to the effector sleeve.

A third lengthwise extending channel may be provided for flushing the closed biopsy cup, to transfer by flushing, a tissue specimen back to the outlet at the proximal end of the third lengthwise extending channel at the proximal tube end, e.g. for the tissue specimen to be collected directly in a tissue vial. marked with patient identification and position on the bladder map. Thus collecting of the tissue specimen is conducted without the need for further human interaction, without the tissue specimen being touched by human, or without other kinds of manipulation of the sample. Further human interaction during biopsying is not excluded within the scope of the present invention but is preferred excluded in the surgical procedure to make this surgical procedure not only more safe in terms of contamination and preserving of the tissue specimen, but also easy to perform and less invasive on the patient and of less pain to the patient. The tissue specimens are not frayed at the edge, need not be taken out of the endosurgical device, be set free from barbs, be cut into smaller pieces, or in any other way be brought in contact with the surrounding environment. The endosurgical device enables a completely closed procedure once the end effector is inside the patient. The vial may e.g. be detachably coupled in fluid communication with the third lengthwise extending channel of the tube via a suitable configured adapter or manifold, or the proximal end of the tube may divide in individual tubes. In case of the tube dividing into individual tubes these are reachable by the surgeon from outside the patient, e.g. at a handle part.

Therefore, the criteria that the maximum exterior diameter of the effector sleeve and/or of the reinforcing member around the tube must not exceed the interior diameter of the endoscopes' working channel need not be observed for the individual tubes outside the patient.

Known forceps devices on the market that use diathermy cause the tissue specimen to be destroyed by the heat and that the tissue specimen stick between the opposite cutting edges of the opposite jaws, so that the tissue specimen has to be manually removed from the forceps. When using the endosurgical device of the present invention the diathermy does not damage the tissue specimen because the tissue specimen so easily releases from the organ and from the exteriorly insulated jaws, and optionally due to the instant cooling of the jaws initiated by the flushing fluid.

One of the opposite jaws may have an opening configured to expose a needle or a nozzle for application of a local anesthetic at one or more target site or local areas wherefrom a tissue specimen is to be resected. When the biopsy cup is closed the needle or nozzle may reciprocate inside the fourth lengthwise extending channel of the tube to allow the needle or nozzle to be retracted into the opening to sealingly close the opening.

Advantageously the needle or nozzle is arranged to be exposed along an axis off set the central axis of the flexible tube.

In a preferred embodiment the opening configured to expose a needle or a nozzle can be provided with a tubular guide member protruding inside the biopsy cup when the jaws are closed. The tubular guide member can keep the tip of the needle or the end of the nozzle out of contact with the tissue specimen and can prevent the needle or nozzle from bending, so that exposure of the needle or nozzle can always be achieved and ensured.

The third lengthwise extending channel can conveniently be used for flushing the closed biopsy cup as described above. To that aspect the third lengthwise extending channel may be in fluid communication with another of the lengthwise extending channels via the biopsy cup defined by the closed opposite jaws. To supply a flushing fluid, such as water, saline or a non-conductive liquid such as glycine, the other lengthwise extending channel may be configured to be connected to a source of flushing fluid and the third lengthwise channel be configured to allow a tissue specimen accommodated inside the biopsy cup to be flushed out of the device by the flushing fluid arriving at the biopsy cup from the other lengthwise extending channel and entering the third lengthwise extending channel. The other lengthwise extending channel may conveniently be an empty second lengthwise extending channel. If the first lengthwise extending channel that holds the electrical cord is also used as the delivery channel for the flushing fluid, the electrical cord must be insulated. Suction can be used instead of flushing.

The third lengthwise extending channel may have a larger cross-section than any of the first, second and/or fourth lengthwise extending channel to promote ejecting the tissue specimen by flushing. Preferably the third lengthwise extending channel may have the largest cross-section possible in view of the dimensions of the other lengthwise extending channels and the overall diameter of the tube.

Tissue specimens should be deep enough to include both lamina propria and muscularis mucosae, i.e. 3-5 mm in depth. The tissue specimen will automatically be pushed by the pressure of the flushing fluid towards the large cross-section of the third lengthwise extending channel and pressed into and along said third lengthwise extending channel because the third lengthwise extending channel is the only channel that allows the tissue specimen to slip inside and pass along with the flushing fluid out of the outlet of the third lengthwise extending channel. When the tissue specimen is subjected to the pressure of the flushing fluid or to suction it may conform slightly to the lumen as regards shape to pass easily through the third lengthwise extending channel.

A jaw of the end effector can in a preferred embodiment be obtained from a conductive pipe piece having a closed nose portion at the second end. The jaw may then be obtained by cutting, e.g. laser cutting, the pipe piece and forcibly deflecting the jaw away from the central axis of the pipe piece. The opposite jaws may then constitute opposite spring members hinged integral with the main tubular body of the pipe piece and the opposite free ends be a biopsy cup end that together define the biopsy cup in form of a temporary receptacle for the tissue specimen when the jaws are closed by the effector sleeve.

Each of the jaws of the end effector can be obtained from a respective conductive pipe piece having a closed nose portion to make two end effector halves that are assembled into the end effector.

For example, can the two end effector halves be made by cutting two separate pipe pieces with hinge members and cup-shaped jaw and welding the main tubular body together. The main tubular body can also be provided with male and/or female coupling means, which male and/or female coupling means may mate closely together after cutting of the appropriate pipe piece parts, even without welding of the main tubular body, so that the biopsy cup can be closed sealingly by the effector sleeve to prevent flushing fluid from being injected into the organ via crevices and/or gaps when a tissue specimen is flushed out.

The exterior diameter of the tube may be as little as less than or equal to 2 mm for the endosurgical device to fit moveably inside a cystoscope, however other kinds of endoscopes may have larger working channels, in which case the exterior diameter of the tube can be as wide as about 2.5 mm, 3 mm, 3.5 mm, 4 mm, 4.5 mm, or even about 5 mm or above. The diameter of any of the lengthwise extending channels is smaller than the tube diameter.

A reinforcing member or tube, such as a coiled member or spiral member, can be used around the tube to make it sufficiently rigid to be moved in and out of the working channel of the endoscope. When using e.g. a reinforcing spiral member or coiled member to add support to the tube, this member may advantageously be encapsulated by an exterior heat shrink tubing or sheath. The heat shrink tubing advantageously seals and insulates the endosurgical device along its length to prevent it from letting out flushing fluid, but also to makes it easy for the endosurgical device to be passed through the working channel due to low friction. A distal end of the reinforcing member may be joined to a proximal end of the effector sleeve to combine the reinforcing member to the effector sleeve to allow the reinforcing member to move the effector sleeve along the tube to open and close the jaws. The exterior heat shrink tubing or sheath may be used to combine effector sleeve and reinforcing member end-to-end.

The flushing pressure of the flushing fluid, or the applied suction, may be set in view of the diameter of the flushing channels of the tube and the size of the tissue specimens so that the tissue specimens are not trapped inside the third lengthwise channel, thus to avoid and prevent plugging of said third lengthwise channel. For an endosurgical device that implements a tube of e.g. 2 mm exterior overall diameter for all functionalities, and being intended for use with a cystoscope, a rather high flushing fluid delivery pressure through the delivering channel, preferably an empty second lengthwise extending second channel, of at least 5 bar may be needed. The fluid delivery pressure may however be as high as 10 bar or 20 bar or even higher. A fluid delivery pressure of e.g. 26 bar has been demonstrated to be satisfactory and efficient.

The free opposite edges of the cup-shaped second ends of the jaws form conductive pinching surface for contacting the tissue diathermally when the jaws are moved towards each other by pulling the effector wire or moving the effector sleeve so that the end effector is arranged inside the effector sleeve. Diathermy remedies the need for the surgeon to pull at the end effector extensively to resect the tissue specimen. He only has to wait a few seconds for the applied heat to set the tissue specimen free at very little discomfort to the patient and with minimum steps for the surgeon. Once the tissue specimen is set free, the force from the effector sleeve makes the jaws of the biopsy cup to close fully, so that the flushing fluid can pass through without the biopsy cup leaks noticeably.

The steps of the surgical procedure using the endosurgical device of the present invention for taking tissues specimens may comprise the steps of a) inserting an endoscope, preferably an endoscope having means o visualize the organ internally, such as a fiber optic means, b) optionally expanding the organ wherefrom tissue specimens are to be resected with liquid supplied through the working channel or other channel of the endoscope, c) inserting the endosurgical device of the present invention into the working channel of the endoscope, optionally if not performed in step b) expanding the organ wherefrom tissue specimens are to be resected with liquid supplied through a lengthwise extending channel of the endosurgical device, d) anesthetizing all areas suspect of cancer, or anesthetizing locally at the sampling site, using the needle or nozzle of the endosurgical device, optionally inducing swelling to facilitate taking the tissue specimen, e) closing the jaws by displacing the end effector inside the effector sleeve to pinch a tissue specimen, f) activating diathermy by providing current via an electrical cord to the end effector to set the tissue specimen free for accommodation inside the biopsy cup, g) flushing the tissue specimen out of the biopsy cup under high fluid pressure, and collecting the tissue specimen at the proximal tube end, preferably collecting the tissue specimen in a formalin-containing vial, h) displacing the end effector out of the effectors sleeve to open the jaws, i) repeating steps e)-h) in case of anesthetizing all areas suspect of cancer, or in case of local anesthesia repeating steps d)-h) until the relevant number of tissue specimens has been taken, j) optionally destroying any remaining areas of cancer by burning function by moving the jaws to the tissue being destroyed, k) withdrawing the endosurgical device, and l) withdrawing the endoscope.

Preferably the organ is the bladder, but other organs can be subjected to same principles and biopsy procedure, e.g. can the organ be the digestive tract, such as the intestine, stomach or esophagus: or the airways, such as the lung.

If excess bleeding occurs diathermy can be repeated locally, as well as step j) can be performed at any stage of the surgical procedure. The diathermy may advantageously be monopolar.

The needle or nozzle associated with the fourth lengthwise extending channel may he utilized for other purposes than anesthesia, such as for delivering the expanding fluid to the organ in step c), inject medication or fluid, such as local anesthesia or adrenaline to stop bleeding. Other options include, but are not limited to, using a surgical laser or a clamp tool through the fourth lengthwise extending channel.

BRIEF DESCRIPTION OF THE DRAWINGS

The invention will now be described with reference to the drawing by way of exemplary embodiments of endosurgical devices of the present invention.

DETAILED DESCRIPTION OF SPECIFIC EMBODIMENTS

Figure 1:
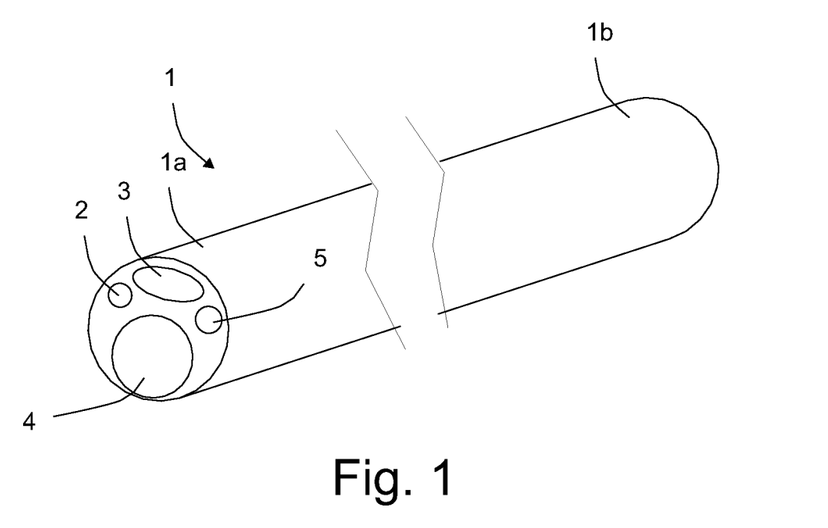
FIG. 1 is a perspective view of a flexible 4-channel tube for use in an endosurgical device of the present invention.

The flexible multi-channel tube 1 seen in FIG. 1 has four lengthwise extending channels 2,3,4,5. The first lengthwise extending channel 2 accommodates an effector wire (not shown), the second lengthwise extending channel 3 serves as a first flushing channel for supplying flushing liquid, such as water, under high pressure to the biopsy cup, the third lengthwise extending channel 4 serves as a second flushing channel for ejecting the tissue specimen by means of the flushing liquid arriving from the second lengthwise extending channel 3, and the fourth lengthwise extending channel 5 accommodates a lengthwise displaceable needle or nozzle (not shown).

Figure 2:
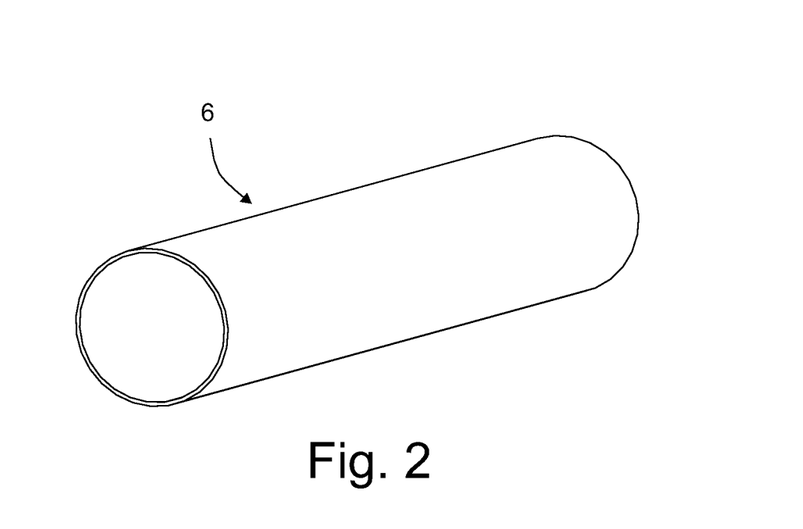
FIG. 2 is a perspective view of an effector sleeve.

The effector sleeve 6 seen in FIG. 2 has an internal diameter selected for the end effector to move tightly in and out of it to open and close the jaws. The effector sleeve 6 may be a metal pipe.

Figure 3:
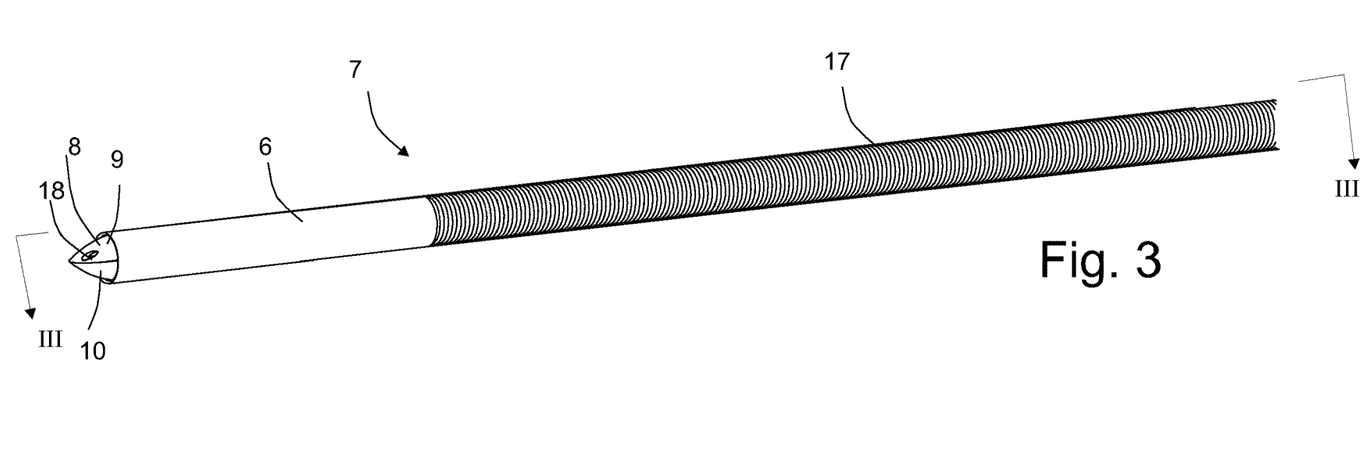
FIG. 3 is a perspective view of the front end part of a first embodiment of an endosurgical
device seen from the side.
Figure 4:
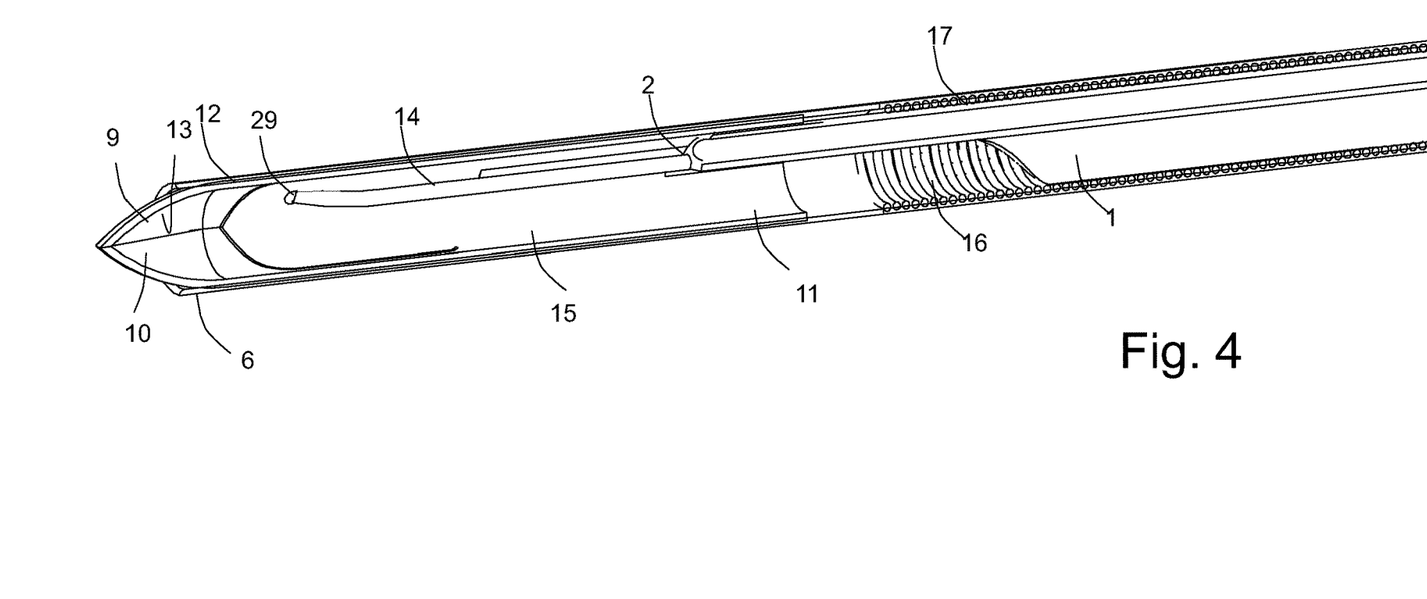
FIG. 4 is a lengthwise enlarged scale sectional view taken along line in FIG. 3.

FIG. 3 is a perspective fragmentary view of the front end part of a first embodiment 7 of an endosurgical device seen from the side, and FIG. 4 is a lengthwise, enlarged scale, sectional view of the same taken along line III-III in FIG. 3.

The endosurgical device 7 has a first embodiment of an end effector 8 accommodated inside the effector sleeve 6 with the opposite jaws 9,10 closed due to the force applied to the jaws 9,10 by said effector sleeve 6. The end effector 8 has a first end 11 in fluid communication with the multi-lumen tube 1 and an opposite second end 12 that includes the opposite first jaw 9 and second jaw 10 that together delimit a biopsy cup 13 in the closed condition of said opposite jaws 9,10.

An electrical cord 14 extends via the first lengthwise extending channel 2 of the tube 1 and is secured to the main tubular body 15 at securing aperture 29 between the first end 11 and the second end 12 of the end effector 8 to heat up the opposite jaws 9,10 when current is applied to the end effector to take the tissue specimen.

The flexible tube 1 is surrounded by a coiled member 16, as seen best in FIG. 4, to reinforce the flexible tube with sufficient flexible rigidity so that it can move inside a working channel of an endoscope (not shown). An exterior plastic tubing 17 is heat-shrunken around the length of the of the endosurgical device to seal joints and insulate the endosurgical device from the working channel, and combining the coiled reinforcing member 16 to the effector sleeve 6, e.g. heat fusion, to enable the effector sleeve to move lengthwise to open and close the jaws 9,10 when needed.

Figures 5, 6:
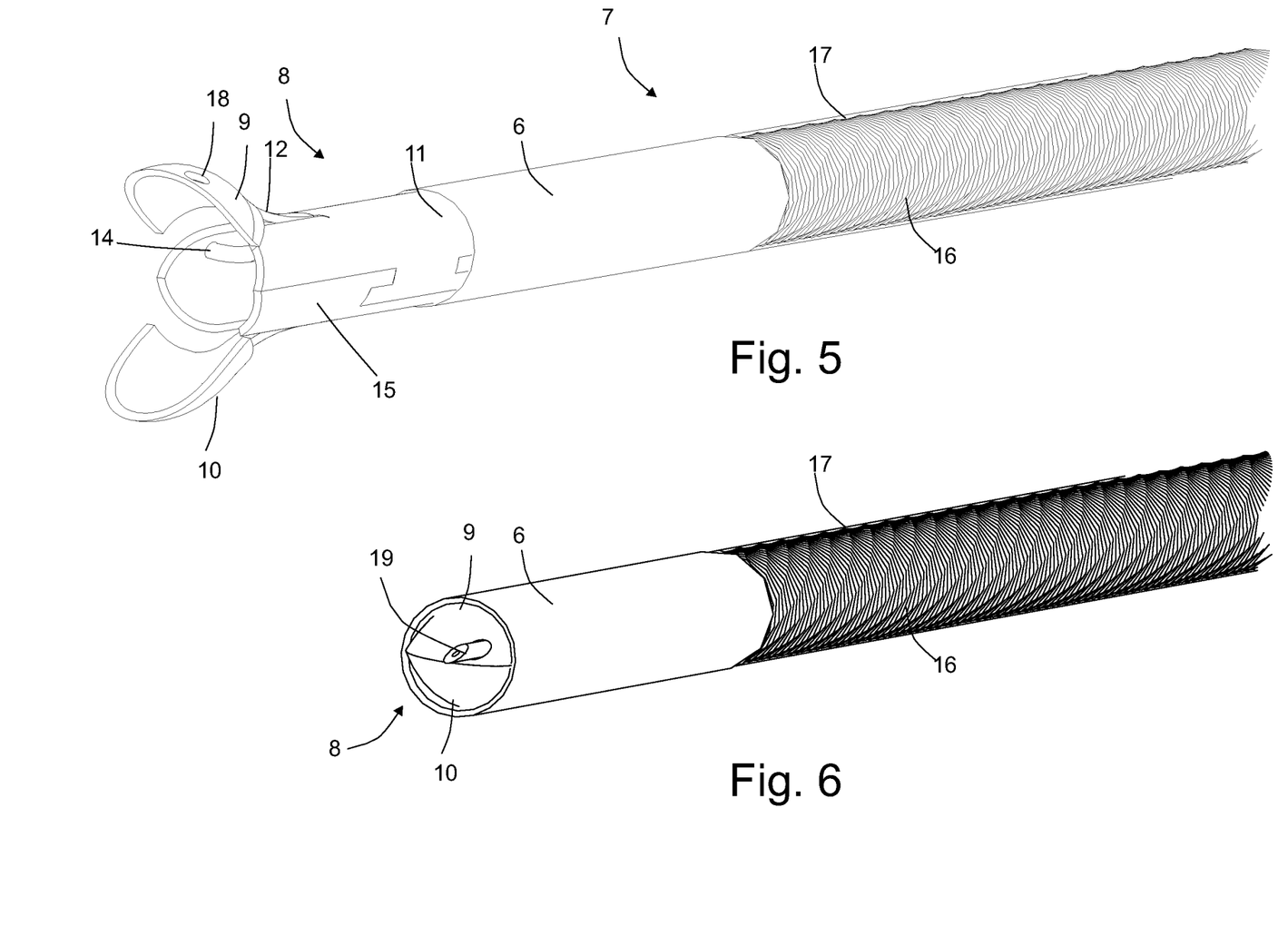
FIG. 5 shows, in an enlarged scale view, the first embodiment of an endosurgical device with open jaws.
FIG. 6 shows the same with closed jaws and exposed needle.

The first jaw 9 has an opening 18 for exposing a needle or nozzle 19, as seen best in FIG. 6, which needle or nozzle extends closely inside the fourth lengthwise extending channel 5 of the tube 1, so that when the needle 19 is retracted it sealingly plugs the opening 18.

Figure 7:
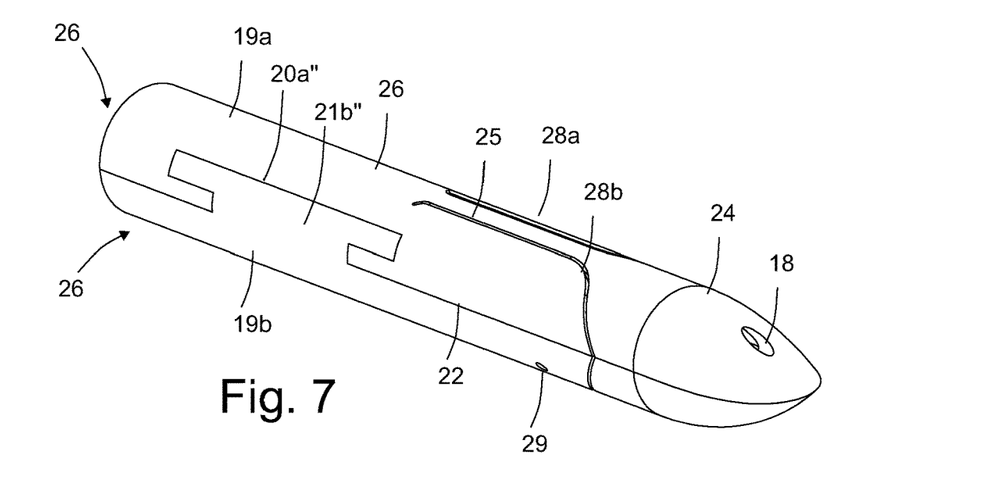
FIG. 7 shows a first embodiment of an end effector made from two pipe piece blanks with tapered noses, and where the jaws are closed.

FIG. 7 shows the first embodiment of an end effector 8 made from two pipe pieces 26 each having a tapered nose 24. Each of the pipe pieces 26 have been cut into two elongate pipe halves 19a,19b along a first cutting line 22, e.g. by laser cutting into a pattern that provides the respective pipe halves 19a,19b with opposite first coupling means 20a'20b' and second coupling means 21a',21b" that, when the opposite pipe halves 19a,19b are subsequently joined to obtain the main tubular body 15 of the end effector 8, said coupling means mate so closely together that leakage along the first assembling line 22 is substantially prevented, and assembling can be done without even welding. Welding or other kinds of fusion of the appropriate parts of the main tubular body is not excluded.

Figure 8:
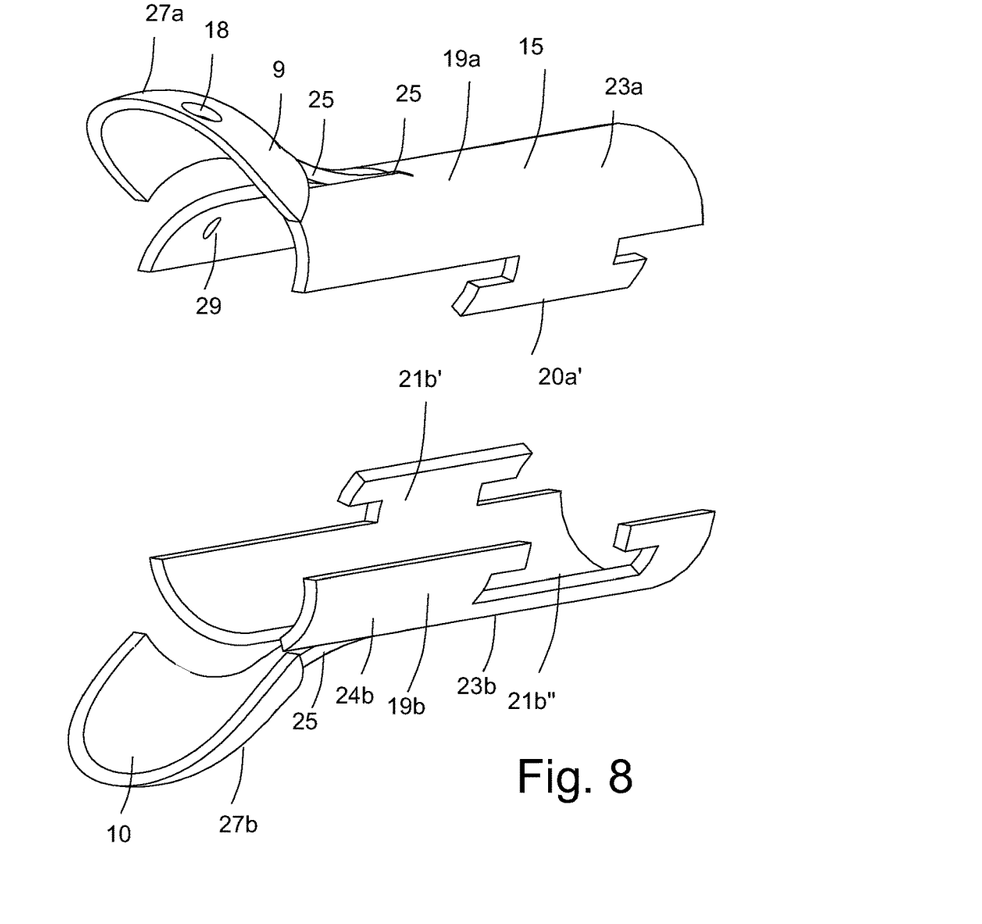
FIG. 8 is an exploded, enlarged scale view of the same with open jaws.
Figure 9:
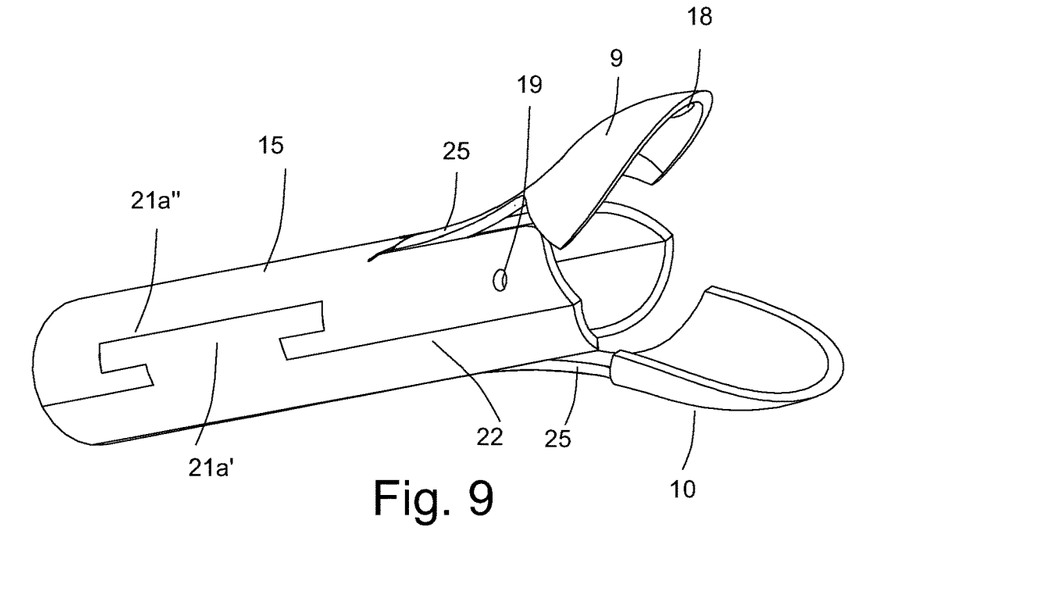
FIG. 9 shows the same in assembled state with the jaws in open position.

As seen in FIGS. 7, 8 and 9 each jaw 9,10 is also sectioned out of the curved pipe walls 23a,23b of the opposite pipe halves 19a,19b, e.g. by laser cutting along second cutting lines 28a,28b. Each jaw 9,10 is thereby shaped with an elongate hinge member 25 emanating from the respective pipe wall 23a,23b and an opposite wider cup-shaped end 27a,27b inherently obtained due to the initially closed tapered nose 24 of the pipe piece 26.

After cutting the respective hinge members 25 are deflected to curve away from each other, as seen in FIGS. 8 and 9. The opposite first coupling means 20a',20b' and second coupling means 21a',21 b" have been mated together, as seen in FIG. 9, where the end effector 8 is in its relaxed state ready to pinch a tissue specimen. When the end effector 8 is retracted inside the effector sleeve 6, or the effector sleeve is displaced distally by displacing the reinforcing member with the effector sleeve in front of it, the opposite jaws 9,10 are forced together, and the end effector 8 reaches the tensioned configuration similar to the configuration seen in FIGS. 3, 4 and 7. The effector sleeve 6 provides further sealing effect along the cutting lines 22;28a,28b. A securing aperture 29 for the electrical cord 14 is provided at the main tubular body 15.

Figure 10:
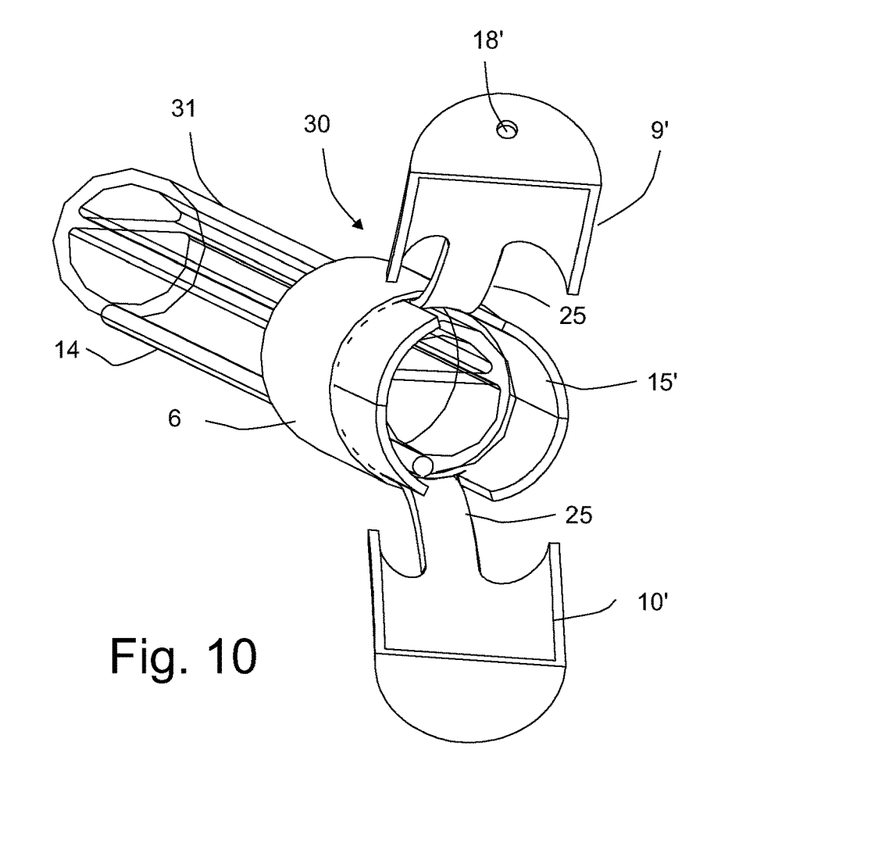
FIG. 10 is a perspective view seen from the front of a second embodiment of an end effector connected to a double-lumen tube.
Figures 11, 12:
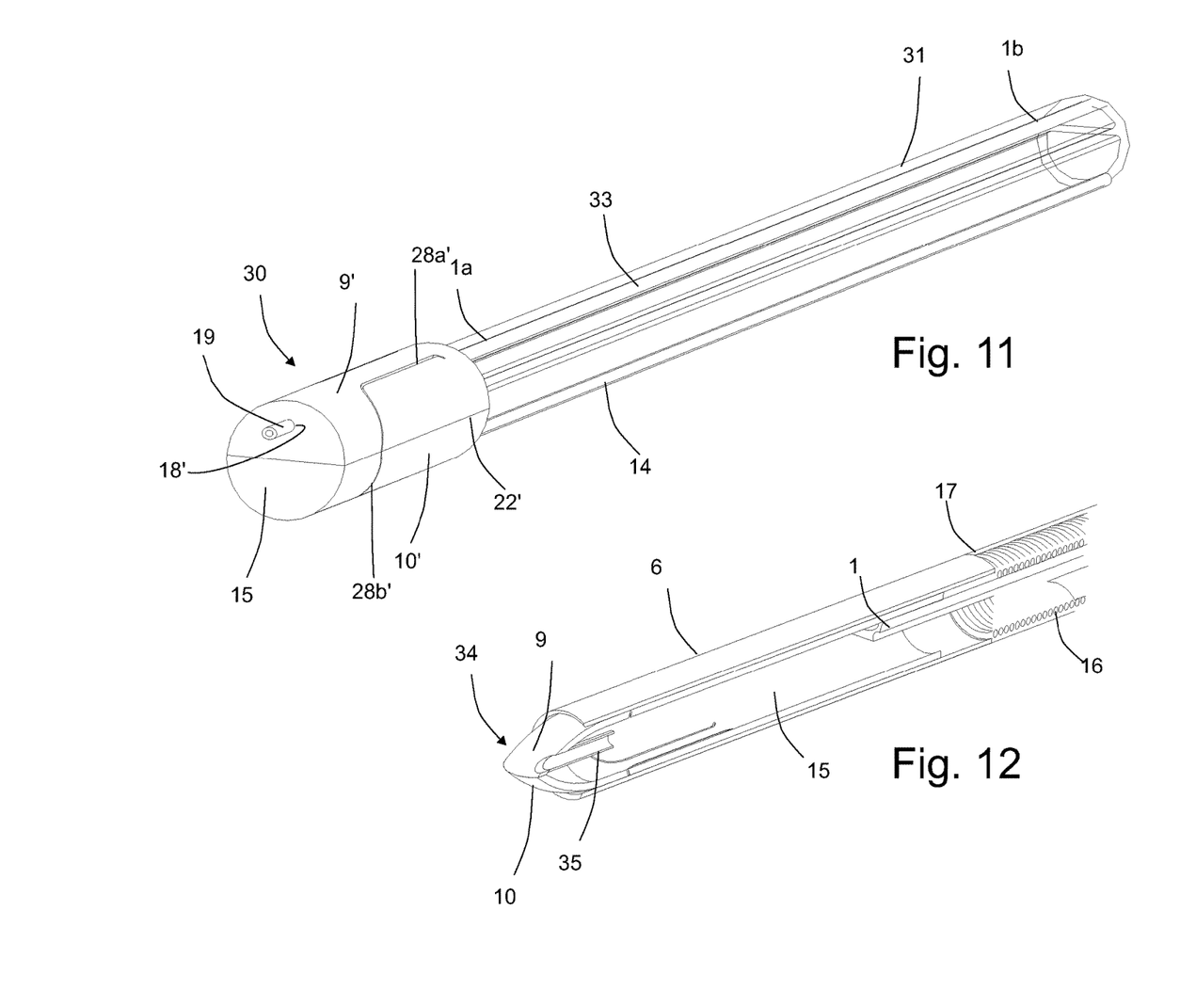
FIG. 11 is a perspective, angled side view of an endosurgical device implementing the end effector seen in FIG. 10 with the jaws seen in closed condition and the needle exposed.
FIG. 12 is a sectional view of a third embodiment of an end effector having a tubular guide member for the nozzle.

FIG. 10 is a perspective view seen from the front of a second embodiment 30 of an end effector connected to a double-lumen tube 31 via an effector sleeve 6. FIG. 11 shows a fragment of the front end part of an endosurgical device implementing the end effector seen in FIG. 10 with the jaws seen in closed condition and the anesthetic needle exposed, but where the effector sleeve 6 has been left out in FIG. 11 to better illustrate the end effector. To illustrate the two lumens of the double lumen tube 31 this tube is shown as transparent and no reinforcing member is shown either.

The second embodiment of an end effector 30 mainly differs from the first embodiment of an end effector 8 in that the nose 24' is flat instead of tapered, as seen in FIG. 11. A flat nose requires less processing during manufacturing in that a pipe piece simply is closed by a flat end plate during molding or by welding. The end effector 30 is cut similarly as described for the first embodiment of an end effector, and the jaws 9',10' made by deflecting the cut hinge members away from each other as also described for the first embodiment of an end effector. A flat-nosed end effector can be made of two separate end-closed pipes cut lengthwise and subsequently joined, or be made from one end-closed pipe.

Using the terminology used for the first embodiment of an end effector and tube the double lumen tube 31 has a fourth lengthwise extending channel 5 for the needle 19 and a third lengthwise extending channel 4 for transporting the tissue specimen out of the tube 31 by flushing or suction. The insulated electric cord 14 extends alongside the wall of the third lengthwise extending channel 4, inside said third lengthwise extending channel 4 of the double lumen tube 31, which third lengthwise extending channel 4 then also serves the purpose of the first lengthwise extending channel 2. Optionally an exterior lengthwise extending recess in the exterior wall of said tube may serve as the first lengthwise extending channel 2. The fourth lengthwise extending channel 5 may also serve the purpose of the second lengthwise extending channel 3 to deliver the flushing fluid to the biopsy cup 13' in the closed condition of the opposite jaws 9',10' where the needle 19 plugs the opening 18' for exposing said needle 19.

For both the first and second embodiment of an endosurgical device the effector wire 33 may be the electrical cord 14 or be separate component.

FIG. 12 is a sectional view of a third embodiment 34 of an end effector having a tubular guide member 34 for controlling the displacing of the needle 19. The tubular guide member 35 guides the needle 19 out of the opening 18 and has a length sufficient to keep the needle tip inside the tubular guide member 35 during an injection stroke.

Figure 13:
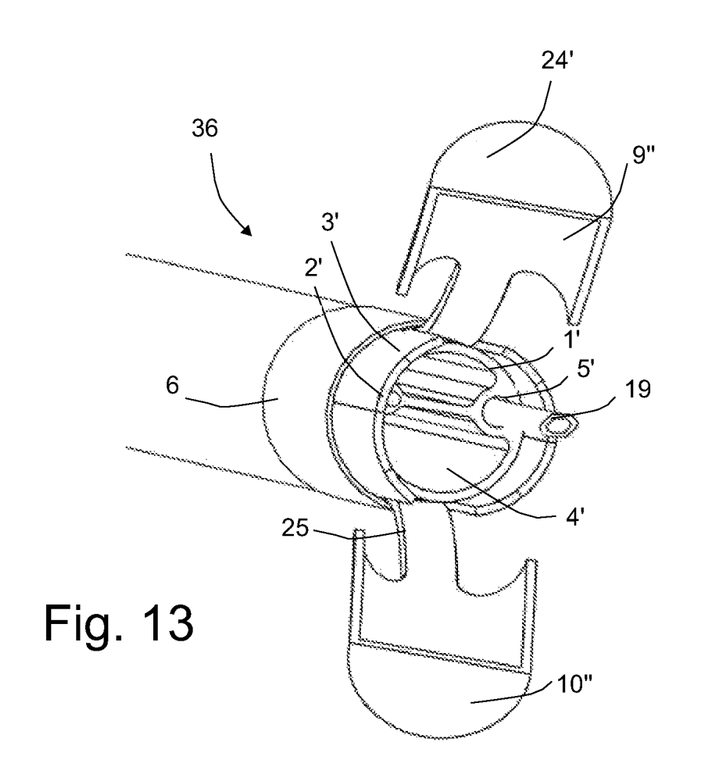
FIG. 13 is a perspective view seen from the front of a fourth embodiment of an end effector mounted to an alternative embodiment of a tube and with open jaws and exposed needle.
Figure 14:
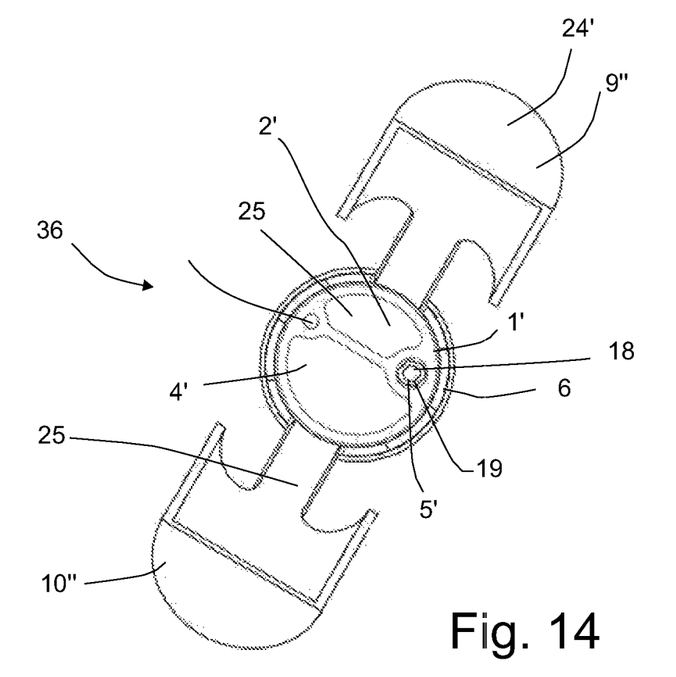
FIG. 14 shows the same in a front end view.

FIG. 13 is a perspective view seen from the front of a fourth end effector 36 with open jaws 9",10' and exposed needle 19 and mounted on an alternative embodiment of a tube F. FIG. 14 shows the same in a front end view. The fourth embodiment of an end effector 36 corresponds substantially to the second embodiment shown in FIGS. 10 and 11 and for like parts same reference numerals are used.

The fourth embodiment of an end effector 36 differs from the second embodiment of an end effector in that the flat nose 24' has no opening 18 through which the needle 19 can be exposed when the jaws 9',10" are closed. Instead the needle 19 is confined within the closed biopsy cup defined by the closed jaws 9',10" of the end effector 36. Once the end effector 36 is set free of the effector sleeve 6, either by retracting the effector sleeve 6 or by pushing the end effector 36 forward out of the distal opening of the effector sleeve 6, the needle can be set free to assume an exposed active position wherein it can be manipulated to apply local anesthetic. To that aspect the active position may be triggered by the needle being spring-biased. To actually conduct a biopsy, the needle 19 may he retracted, the opposite jaws closed around the selected tissue, diathermy applied, and the cut tissue specimen flushed through the tube 1' towards the handle of the endoscope used together with the endosurgical device with the end effector 36.

The alternative tube corresponds substantially to the first embodiment of a tube 1 and for like part same reference numerals are used. The alternative tube 1' differs only slightly from the first embodiment of a tube 1 in that the diameters and cross-sections of the lengthwise extending channels 2',3',4',5' differ. In particular, the second lengthwise extending channel 3' that serves as a first flushing channel for supplying flushing liquid, such as water, under high pressure to the closed biopsy cup, and the third lengthwise extending channel 4, that e.g. serves as a second flushing channel for ejecting the tissue specimen by means of the flushing liquid arriving from the second lengthwise extending channel 3, are larger or serves for application of suction.

As for the first embodiment of an endosurgical device 7, a second embodiment of an endosurgical device implementing any embodiment of an end effector 30;34;36, and any kind of multi-lumen tube 1,1' can be reinforced by a coiled reinforcing member, the effector sleeve be end-to-end connected to a coiled reinforcing member, and a heat-shrink tubing 17 be applied exteriorly, as described above.

The endosurgical device of the present invention suggests a whole new way to take biopsies from a hollow organ. Completely new conditions are created for the treatment of these patients. The costs can be drastically reduced and the patient benefit is extremely high. It will be possible to diagnose and correct outpatients with cancers in a few minutes on a regular visit. Patients no longer need any catheter treatment after surgery, which means they eliminate the high risk of urinary tract infection that a catheter entails. All different categories of staff no longer need to be involved; it is enough with a doctor and nurse, which means a huge cost reduction, and patients can receive cancer treatment much faster, and surgical capacity for other purposes are released.

The invention claimed is:
1. An endosurgical device, comprising:
 a flexible tube having a distal tube end, a proximal tube end, and at least two lengthwise extending channels, an end effector comprising two opposite jaws having opposite cutting edges, wherein the end effector is provided at the distal tube end, and an effector sleeve that surrounds the flexible tube at least at the distal tube end, and means for reciprocating the end effector axially in relation to the effector sleeve, or vice versa, to open and close the jaws; wherein the end effector of the endosurgical device comprises a main tubular body having a first end connected to the distal tube end to provide fluid communication to the at least two lengthwise extending channels, and an opposite second end having the opposite jaws, at least one of the jaws is arranged to diverge from a longitudinal axis of the end effector in a relaxed condition when the end effector is at least partly outside the effector sleeve, the end effector and the jaws are arranged so that the jaws are subjected to a compression force by the effector sleeve to keep the gap between the jaws closed to define a closed biopsy cup when the end effector is at least partly inside the effector sleeve, and the exterior faces of the opposite jaws are electrically insulated; and an electrical cord for providing current to the end effector extends inside one of the lengthwise extending channels;

wherein the tube has at least a first lengthwise extending channel for an effector wire for controlling the end effector when the end effector moves in and out of the effector sleeve, optionally the effector wire is the electrical cord for applying current to the end effector, alternatively the tube has a separate second lengthwise extending channel for accommodating the electrical cord;

wherein the tube has a third lengthwise extending channel for transferring a tissue specimen out of the closed biopsy cup by flushing with a fluid; and wherein one of the opposite jaws has a wall with an opening configured to expose a needle or a nozzle for application of a local anesthetic at a target site when the biopsy cup is closed, and wherein the needle or nozzle is reciprocatingly arranged inside a fourth channel of the tube to allow the needle or nozzle to be retracted into the opening to sealingly close the opening in the jaw wall, optionally a tubular guide member protrudes from the opening inside the closed biopsy cup defined by the closed opposite jaws to control axial movement of the needle.

2. The endosurgical device according to claim 1, wherein the third lengthwise extending channel has a larger cross-section than at least any of the first and the fourth lengthwise extending channel.

3. An endosurgical device according to claim 1 further comprising a tubular guide member protruding from the opening inside the closed biopsy cup defined by the closed opposite jaws to control axial movement of the needle.

4. An endosurgical device according to claim 1, wherein the third lengthwise extending channel has a larger cross-section than at least any of the first and the fourth lengthwise extending channel.

5. An endosurgical device, comprising:

a flexible tube having a distal tube end, a proximal tube end, and at least two lengthwise extending channels, an end effector comprising two opposite jaws having opposite cutting edges, wherein the end effector is provided at the distal tube end, an effector sleeve that surrounds the flexible tube at least at the distal tube end, and means for reciprocating the end effector axially in relation to the effector sleeve, or vice versa, to open and close the jaws, wherein the end effector of the endosurgical device comprises a main tubular body having a first end connected to the distal tube end to provide fluid communication to the at least two lengthwise extending channels, and an opposite second end having the opposite jaws, at least one of the jaws is arranged to diverge from a longitudinal axis of the end effector in a relaxed condition when the end effector is at least partly outside the effector sleeve, the end effector and the jaws are arranged so that the jaws are subjected to a compression force by the effector sleeve to keep the gap between the jaws closed to define a closed biopsy cup when the end effector is at least partly inside the effector sleeve, the exterior faces of the opposite jaws are electrically insulated, an electrical cord for providing current to the end effector extends inside one of the lengthwise extending channels, and wherein one of the opposite jaws has a wall with an opening configured to expose a needle or a nozzle for application of a local anesthetic at a target site when the biopsy cup is closed, and wherein the needle or nozzle is reciprocatingly arranged inside a fourth channel of the tube to allow the needle or nozzle to be retracted into the opening to sealingly close the opening in the jaw wall.

* * * * *

UNITED STATES PATENT AND TRADEMARK OFFICE
CERTIFICATE OF CORRECTION

| | |
|---|---|
| PATENT NO. | : 11,547,470 B2 |
| APPLICATION NO. | : 16/955725 |
| DATED | : January 10, 2023 |
| INVENTOR(S) | : Robert Axelsson et al. |

It is certified that error appears in the above-identified patent and that said Letters Patent is hereby corrected as shown below:

In the Claims

Claim 1, Line 15, of Column 13 "at least one ofthejaws is arranged to diverge from a" should be -- at least one of the jaws is arranged to diverge from a --

Signed and Sealed this
Eighteenth Day of July, 2023

Katherine Kelly Vidal
*Director of the United States Patent and Trademark Office*